United States Patent [19]

Niederau et al.

[11] 4,399,227

[45] Aug. 16, 1983

[54] PROCESS FOR DETERMINATION OF GLYCOSYLATED HEMOGLOBIN AND REAGENT THEREFOR

[75] Inventors: Cornelia Niederau, Wuppertal; Hans Reinauer, Düsseldorf, both of Fed. Rep. of Germany

[73] Assignee: Panchem Gesellschaft für chemische Produkte mbH, Fed. Rep. of Germany

[21] Appl. No.: 350,181

[22] Filed: Feb. 19, 1982

[30] Foreign Application Priority Data

May 13, 1981 [DE] Fed. Rep. of Germany ....... 3119046

[51] Int. Cl.$^3$ ...................... G01N 33/66; G01N 33/72
[52] U.S. Cl. ........................................ 436/67; 436/175
[58] Field of Search .................... 436/67, 89, 90, 111, 436/175

[56] References Cited

PUBLICATIONS

Nathan et al., Diabetes, 30:700–701, Aug. 1981.
Innanen et al., Clinical Chemistry, vol. 27, No. 8, 1981, pp. 1478–1479.
Nathan, Clinical Chemistry, vol. 27, No. 7, 1981, pp. 1261–1263.

*Primary Examiner*—Arnold Turk
*Attorney, Agent, or Firm*—Burns, Doane, Swecker & Mathis

[57] ABSTRACT

An improved process for determining glycosylated hemoglobin wherein the contribution of unstable glucose-aldimine-hemoglobin compounds to the HbA$_1$ value is substantially eliminated by reacting the hemolysate with a primary amine and a hydrazine compound and thereafter subjecting the hemolysate to chromatography. The process enables reliable evaluation of the HbA$_1$ value as a long-term parameter in diabetic metabolism control.

27 Claims, No Drawings

PROCESS FOR DETERMINATION OF GLYCOSYLATED HEMOGLOBIN AND REAGENT THEREFOR

TECHNICAL FIELD OF THE INVENTION

The invention provides an improved process for determination of glycosylated hemoglobin and a reagent useful in the subject process.

BACKGROUND ART

The fact that in diabetic patients an increase in the glycohemoglobin content of the erythrocytes takes place affords a method of determination useful in the control of the metabolism of diabetic patients. Through a nonenzymatic, irreversible reaction of glucose in the blood with one of the terminal amino groups of the protein chains and with the $\epsilon$-amino group of lysine, glycosylated hemoglobin fractions are formed in the erythrocytes. These fractions may be separated by means of chromatography from normal hemoglobin. The glycoprotein synthesis takes place over the entire half-life period of 120 days of the erythrocytes, with the reaction being a function of the average glucose concentration and its duration in the blood. The total $HbA_1$ glycohemoglobin fraction consists of three subfractions, $HbA_{1a} + HbA_{1b} + HbA_{1c}$. The glycosylated hemoglobin designated by $HbA_{1c}$ is particularly well-suited for the control of blood sugar. The $HbA_{1c}$ content, which is present in an amount of 3–6% in the total hemoglobin of normal adults, is therefore an indication of the average level of blood sugar over the life of the erythrocytes. The determination of the value of $HbA_{1c}$ is effected after hemolysis of the erythrocytes, such as by means of chromatographic separation of the hemoglobin fractions in macrocolumns [Trivelli et al., *New Engl. J. Med.* 284, 353–357 (1971)] or in microcolumns and subsequent colorimetric measurements in a spectrophotometer at approximately 415 nm.

Separation by means of microcolumns has largely superseded the macrocolumn method, which is expensive in practice, since it has been determined that the total fraction of the glycosylated hemoglobin $HbA_{1a+1b+1c}$ also affords the long-term or chronic blood sugar value in a good correlation; accordingly, the separation of the subfractions, which is not possible in microcolumns, may be eliminated for diagnostic purposes [Koening, R. J., C. M. Peterson, R. L. Jones, C. Saudek, M. Lehrman and A. Cerami, "Correlation of glucose regulation and hemoglobin $A_{1c}$ in diabetes mellitus", *N. Eng. J. Med.* 295, 417–420 (1976); Fitzgibbons, J. F., F. D. Koler and R. T. Jones, "Red cell age-related changes of hemoglobins $A_{1a+b}$ and $A_{1c}$ in normal and diabetic subjects", *J. Clin. Inves.* 58, 820–824 (1976)].

All of the commerically available microcolumn determination sets of the various manufacturers use the same fundamental technique. The $HbA_1$ total fraction is separated from the residual hemoglobin by means of an ion exchanger, with the aid of a buffer with its pK value adjusted to the ionic strength of the exchanger. As the reference value, the residual hemoglobin is then washed from the column with a second elution solution, or the total hemoglobin is determined from a corresponding hemolysate aliquot. The relative proportion of the $HbA_1$ fraction is then calculated for the total hemoglobin from both values. Fundamentally, methods of determination wherein the hemoglobin bonded to the exchange resin is removed by centrifugation are also based on this technique (for example, Leeco Diagnostics).

It is known that the glycosylation of hemoglobin in the erythrocytes takes place by a two-stage process, wherein among others, initially the aldehyde group of the glucose reacts with the amino group of the terminal valine of the $\beta$-chain of the hemoglobin to give the aldimine form (Schiff base). This relatively unstable aldimine derivative is then rearranged by means of an Amadori transposition into the relatively stable ketoamine form. Short term blood sugar fluctuations during the day on which the test is performed may thus lead to a correspondingly high rate of the formation of the unstable aldimine, which could render the evaluation of the $HbA_1$ value as a long-term parameter of diabetic metabolism control questionable. See Schernthaner, *Dtsch. Med. Wschr.* 106, 259–261 (1981); J. Ditzel, *Diabetologia* 19, 403–404 (1980).

BRIEF SUMMARY OF THE INVENTION

It is the object of the present invention to improve the above-described methods for the determination of $HbA_1$, by eliminating the unstable aldimine form prior to separation of the hemoglobin fractions.

It has now been found surprisingly that it is possible, in a simple manner, to substantially eliminate the unstable aldimine form of the $HbA_1$ fraction by means of a competing amount of a primary amine, in the presence of a hydrazine compound, while forming the corresponding Schiff base compound in a "transschiffizing reaction", with the resulting Schiff base compound no longer interfering with the determination of the stable glucose-ketoamine form of hemoglobin in chromatographic separations and spectroscopic measurements. Thus, the present invention provides an improved process for the determination of the glycosylated hemoglobin content of a blood sample comprising the hemolysis of erythrocytes, the chromatographic separation of hemoglobin fractions and their colorimetric measurement, wherein the contribution of unstable glucose-aldimine-hemoglobin compounds to the $HbA_1$ value is substantially eliminated by reacting the hemolysate with a primary amine and a hydrazine compound and thereafter subjecting the hemolysate to chromatography.

DETAILED DESCRIPTION OF THE INVENTION

In accordance with the present invention, any of the water-soluble amines having at least one free $NH_2$ group, such as, for example, hydroxylamine, alkylamines (such as ethylamine or propylamine), hydroxyalkylamines (such as ethanolamine) or the amino acids, are suitable for use as the primary amine. Lysine and valine are particularly suitable among the amino acids. Pyridoxamine or aniline may also be used. Among the hydrazine compounds, hydrazine itself and its substituted compounds, such as phenylhydrazine, semicarbazide, and the like are suitable.

Preferably, the addition of the combination of the primary amine and the hydrazine compound is effected in the hemolysis stage of the erythrocytes which is necessary to set free the hemoglobin, by using a hemolysis reagent containing both the primary amine and the hydrazine compound.

A preferred reagent of the present invention is illustrated by the following example. However, this example is in no way limitative of the remainder of the specification and claims, as many modifications in materials and methods will be apparent to those skilled in the art.

EXAMPLE

An especially suitable reagent for use in the subject process contains the following components:
200 mM semicarbazide hydrochloride
20 mM lysine
20 mM valine
50 mM phosphate buffer (pH=6.6) and
0.813 mM digitonin
per liter of the aqueous reagent solution.

In general, freshly extracted blood should be used to effect the determination of the $HbA_1$ value according to the invention. If this is not possible, it is preferable that heparin or ethylenediaminetetraacetic acid should be added to the blood as an anticoagulant; such does not interfere with the determination. Blood stabilized in this manner may be stored for a maximum of one week in a refrigerator. Subsequently, the hemolysis reagent containing, according to the invention, the primary amine and the hydrazine compound, is added to the blood, which should be at approximately room temperature (about 20° to 23° C.), followed by brief mixing. After approximately 10 minutes at room temperature, during which time the hemolysis and cleavage according to the invention of the unstable aldimine compounds takes place, the hemolyzed blood is placed, in a manner known per se, on a conventional separating column and the hemoglobin fractions are separated from each other. The fast running fraction ($HbA_1$) is then determined photometrically.

Except for replacing the hemolysis reagent specified by the manufacturer with the reagent according to the invention, the working instructions of the manufacturer can essentially be followed. In the case of blood sugar values of less than 500 ml/dl, the reagent according to the invention is conveniently diluted with an equal volume of distilled water and added in the amount specified by the manufacturer, while also retaining the volume of the blood sample. In the case of blood sugar values in excess of 500 ml/dl, initially one-half of the hemolysis reagent volume required is typically replaced by the concentrated form of the reagent according to the invention and after approximately 10 minutes a corresponding volume of distilled water added.

The content of glycolysated hemoglobin is determined in accordance with the specific working instructions of the system. Due to the elimination, according to the invention, of the unstable aldimine intermediate product of the glycosylating reaction of the hemoglobin erythrocytes, the value measured represents exclusively the content of the stable ketoamine form of the glycosylated hemoglobin, corresponding to the *long-term* value of the blood sugar level, free of short-term fluctuations. This makes it possible to effect a substantially better and safer control and adjustment of diabetic patients in comparison with the chromatographic-photometric determination of hemoglobin practiced heretofore. Postprandial analyses are also possible without interference.

The experiment presented hereinbelow demonstrates the efficacy of the elimination of the unstable aldimine form by the reagent according to the invention.

The glycosylated hemoglobin content was determined in the blood after fasting of 4 different diabetic patients. Corresponding blood samples were incubated for 2 hours with additional glucose in an amount of 50 mM at 37° C. and then the measurement repeated, wherein the testing was effected with (a) a normal hemolysis reagent (0.813 mM digitonin/liter-phosphate buffer, pH=6.6) and (b) with the reagent according to the invention as specified in the Example above.

The table hereinbelow shows the content of glycosylated hemoglobin determined with respect to total hemoglobin.

TABLE

| Initial values of glucose-hemoglobin | 6.73% | 9.5% | 11.1% | 11.86% |
|---|---|---|---|---|
| (a) Glucose-hemoglobin after 2 hours of glycosylation with a conventional hemolysis reagent | 8.75% | 11.9% | 14.3% | 15.16% |
| (b) Glucose-hemoglobin after 2 hours of glycosylation with the reagent according to the invention | 7.66% | 10.5% | 11.16% | 11.81% |

It can be seen that the high values of glucose-hemoglobin measured after artificial hyperglycemia were returned to their initial values as the intermediate unstable aldimine form was eliminated by the reagent according to the invention. The increased glucose-hemoglobin values measured in spite of this, especially in the case of low initial values, indicate that during the glycolysation a portion of the unstable aldimine form has already been rearranged in the stable ketoamine form.

From the foregoing description, one of ordinary skill in the art can easily ascertain the essential characteristics of the present invention, and, without departing from the spirit and scope thereof, can make various changes and/or modifications of the instant invention to adapt it to various usages and conditions. As such, these changes and/or modifications are properly, equitably and intended to be, within the full range of equivalence of the following claims.

What we claim is:

1. In a process for the determination of the glycosylated hemoglobin content of a blood sample comprising the hemolysis of erythrocytes, the chromatographic separation of hemoglobin fractions and their colorimetric measurement, the improvement wherein the contribution of unstable glucose-aldimine-hemoglobin compounds to the $HbA_1$ value is substantially eliminated by reacting the hemolysate with a primary amine and a hydrazine compound and thereafter subjecting the hemolysate to chromatography.

2. A process according to claim 1, wherein the hemolysis and the reaction with a primary amine and a hydrazine compound are carried out simultaneously.

3. A process according to claim 1, or 2, wherein the primary amine comprises hydroxylamine, an alkylamine, a hydroxyalkylamine, an amino acid, aniline or pyridoxamine.

4. A process according to claim 3 wherein the primary amine comprises hydroxylamine.

5. A process according to claim 3 wherein the primary amine comprises an alkylamine.

6. A process according to claim 5 wherein the primary amine comprises ethylamine or propylamine.

7. A process according to claim 3 wherein the primary amine comprises a hydroxyalkylamine.

8. A process according to claim 7 wherein the primary amine comprises ethanolamine.

9. A process according to claim 3 wherein the primary amine comprises an amino acid.

10. A process according to claim 9 wherein the primary amine comprises lysine.

11. A process according to claim 9 wherein the primary amine comprises valine.

12. A process according to claim 9 wherein the primary amine comprises a mixture of lysine and valine.

13. A process according to claim 1 or 2 wherein the hydrazine compound comprises hydrazine, phenylhydrazine or semicarbazide.

14. A process according to claim 13 wherein the hydrazine compound comprises hydrazine.

15. A process according to claim 13 wherein the hydrazine compound comprises phenylhydrazide.

16. A process according to claim 13 wherein the hydrazine compound comprises semicarbazide.

17. A process according to claim 3 wherein the hydrazine compound comprises hydrazine, phenylhydrazine or semicarbazide.

18. A process according to claim 9 wherein the hydrazine compound comprises hydrazine, phenylhydrazine or semicarbazide.

19. A process according to claim 10 wherein the hydrazine compound comprises hydrazine, phenylhydrazine or semicarbazide.

20. A process according to claim 11 wherein the hydrazine compound comprises hydrazine, phenylhydrazine or semicarbazide.

21. A process according to claim 12 wherein the hydrazine compound comprises hydrazine, phenylhydrazine or semicarbazide.

22. In a process for the determination of the glycosylated hemoglobin content of a blood sample comprising the hemolysis of erythrocytes, the chromatographic separation of hemoglobin fractions and their colorimetric measurement, the improvement wherein the contribution of unstable glucose-aldimine-hemoglobin compounds to the $HbA_1$ value is substantially eliminated by reacting the hemolysate with hydroxylamine, an alkylamine, a hydroxyalkylamine or an amino acid and a hydrazine compound and thereafter subjecting the hemolysate to chromatography.

23. A process according to claim 22 wherein the hydrazine compound is hydrazine.

24. A process according to claim 22 wherein the hydrazine compound is phenylhydrazine.

25. A process according to claim 22 wherein the hydrazine compound is semicarbazide.

26. A reagent for use in the process according to claim 2, said reagent comprising lysine, valine, semicarbazide and digitonin in amounts effective to substantially eliminate the contribution of unstable glucose-aldimine-hemoglobin compounds to the $HbA_1$ value, together with sufficient phosphate buffer to establish a pH value of approximately 6.6.

27. A reagent according to claim 22, said reagent containing 20 mM lysine, 20 mM valine, 200 mM semicarbazide hydrochloride, 50 mM sodium phosphate buffer (for pH 6.6) and 0.813 mM digitonin per liter of aqueous solution.

* * * * *